(12) United States Patent
Essers et al.

(10) Patent No.: US 9,481,739 B2
(45) Date of Patent: Nov. 1, 2016

(54) GLUCAN FIBRE

(71) Applicant: Nederlandse Organisatie voor toegepast—natuurwetenschappelijk onderzoek TNO, Delft (NL)

(72) Inventors: Maurice Karel Hubertina Essers, Delft (NL); Johannes Wilhelmus Timmermans, Delft (NL); Jerome Villarama Diaz, Delft (NL); Ronald Tako Marinus van den Dool, Delft (NL); Theodoor Maximiliaan Slaghek, Delft (NL)

(73) Assignee: NEDERLANDSE ORGANISATIE VOOR TOEGEPAST-NATUURWETENSCHAPPELIJK ONDERZOEK TNO, Delft (NL)

( * ) Notice: Subject to any disclaimer, the term of this patent is extended or adjusted under 35 U.S.C. 154(b) by 0 days.

(21) Appl. No.: 14/398,251

(22) PCT Filed: May 21, 2013

(86) PCT No.: PCT/NL2013/050371
§ 371 (c)(1),
(2) Date: Oct. 31, 2014

(87) PCT Pub. No.: WO2013/176542
PCT Pub. Date: Nov. 28, 2013

(65) Prior Publication Data
US 2015/0111848 A1    Apr. 23, 2015

(30) Foreign Application Priority Data
May 21, 2012 (EP) ..................................... 12168724

(51) Int. Cl.
| C08B 37/00 | (2006.01) |
| A23L 1/308 | (2006.01) |
| A23L 1/09  | (2006.01) |
| C12P 19/04 | (2006.01) |
| C12P 19/14 | (2006.01) |

(52) U.S. Cl.
CPC ............ *C08B 37/0009* (2013.01); *A23L 1/095* (2013.01); *A23L 1/308* (2013.01); *A23L 1/3088* (2013.01); *C12P 19/04* (2013.01); *C12P 19/14* (2013.01); *A23V 2002/00* (2013.01); *A23V 2200/00* (2013.01)

(58) Field of Classification Search
None
See application file for complete search history.

(56) References Cited

U.S. PATENT DOCUMENTS

| 2,719,179 A | 9/1955 | Mora et al. |
| 6,559,302 B1 | 5/2003 | Shah et al. |
| 2006/0149053 A1* | 7/2006 | Antrim ................... C08B 30/18 536/123 |

FOREIGN PATENT DOCUMENTS

| EP | 2151500 | 2/2010 |
| WO | 87/07275 | 12/1987 |

OTHER PUBLICATIONS

Cargill, Clearsweet 95% Refined Liquid Dextrose Corn Syrup Product Information, Aug. 14, 2012.*
International Search Report issued in PCT Application No. PCT/NL2013/050371.

* cited by examiner

*Primary Examiner* — Layla Berry
(74) *Attorney, Agent, or Firm* — Lucas & Mercanti, LLP (57) ABSTRACT

Method for preparing a branched glucan having a chain comprising a plurality of glucose units linked by alpha 1,4-glycoside bonds and a plurality of side-groups linked to said chain via another type of glycoside bonding, which side-groups comprise one or more glucose units, the method comprising contacting a glucose source with a polysaccharide—which polysaccharide is a glucan comprising a plurality of glucose units linked by alpha 1,4-glycoside bonds and is essentially linear or branched to a lesser extent than the branched glucan that is to be prepared—in the presence of an acid catalyst under polycondensation conditions, thereby forming the branched glucan.

19 Claims, 4 Drawing Sheets

L# GLUCAN FIBRE

CROSS-REFERENCE TO RELATED APPLICATIONS

This application is a 371 of PCT/NL2013/050371, filed May 21, 2013, which claims the benefit of European Patent Application No. 12168724.8, filed May 21, 2012, the contents of each of which are incorporated herein by reference.

FIELD OF THE INVENTION

The invention relates to a method for preparing a branched glucan, to a branched glucan, and to a use of a branched glucan.

BACKGROUND OF THE INVENTION

Carbohydrates form an important ingredient of various nutrition. They can generally be distinguished in fast (release) carbohydrates, slow (release) carbohydrates and resistant carbohydrates. The fast and slow carbohydrates are digestible carbohydrates, i.e they are digested in the stomach/small intestines. To these categories belong mainly starch and their derivates, e.g. hydrolysates and sugars.

The glycaemic index (GI) is a measure of the effects of carbohydrates on blood sugar levels. The slow digestible carbohydrates provide a lower glycaemic index than the fast digestible carbohydrate. A lower glycaemic index is an indication for slower rates of digestion and absorption of the foods' carbohydrates and may also indicate greater extraction from the liver and periphery of the products of carbohydrate digestion. A lower glycaemic response usually equates to a lower insulin demand but not always, and may improve long-term blood glucose control and blood lipids. The insulin index is also useful for providing a direct measure of the insulin response to a food.

Resistant carbohydrate is not digested in the small intestine. Resistant carbohydrates contribute to the total dietary fibre. Examples of resistant carbohydrates are, resistant starches (Type I to III), fructooligosaccharides, galactooligosaccharides and polydextrose. Some of these can be fermented by microflora in the colon, such as fructoologosacharides and galactoologosaccharides. Resistant carbohydrates that provide nutrition to the microflora may contribute to specific changes in the composition and/or activity in the gastrointestinal microflora that confers benefits upon host well-being and/or health. These are commonly referred to as prebiotics. Examples of prebiotics are fructooligosaccharides and galactooligosaccharides.

Research over the last decades, pointed out a relationship between dietary fibre and the prevention of certain diseases, for example the prevention of diabetes type II. Different prebiotic carbohydrates have different effects on the microflora and/or may offer different health benefits. For example, prebiotics that are fermented relatively quickly may mainly provide nourishment to bacteria in the proximal part of the colon, whereas prebiotics that are fermented relatively quickly may mainly provide nourishment to bacteria in the distal part of the colon. Thus, be selecting a type of prebiotic it may be possible to selectively target microflora in a specific part of the colon. Also different prebiotics may give rise to the formation of different break-down products (different organic acids).

Various technologies have been described relating to the preparation of polysaccharides with potential dietary benefits.

U.S. Pat. No. 6,559,302 relates to a method to prepare an edible polysaccharide wherein a glucose source is reacted with another polyol, such as sorbitol in the presence of a mineral acid. It is not mentioned to use at least two different carbohydrates as a starting material, wherein one is a glucose source selected from glucose, maltose and polydextrose with a polysaccharide (different from said glucose source)—which polysaccharide is a glucan. It is apparent that the used starting materials are all relatively small molecules (dextrose and sorbitol) and there is no suggestion that it would be possible to prepare a branched glucan by polycondensation using a polysaccharide, let alone a polysaccharide that has a polymerisation degree high enough to make it pregelatinisable, or a polysaccharide with a high degree of polymerisation whereby it is not meltable in pure form, due to decomposition at a temperature below its (hypothetical) melting point.

EP 2 151 500 A1 relates to an enzymatic method for the preparation of a branched glucan with water soluble fibre properties with a significantly low-digestibility and effects of inhibiting the elevation of blood sugar level. According to the description, the enzymatically prepared glucan is different from glucans formed in a chemical reaction making use of glucose that is polymerised. In particular, the glucan is characterised by a specific methylation analysis. It is further mentioned that the glucan is hardly digestible by salivary alpha amylase or alpha amylase from pancreas or small intestines, and does not induce acid fermentation in the mouth.

When formulated in a nutritional composition, carbohydrates, in particular fibres and digestible polysaccharides, may also affect other properties of the composition, such as organoleptic effects (e.g. mouth-feel, texture), of the composition, or rheological properties of the composition, such as viscosity. In particular, there is a need for carbohydrates with a relatively low caloric value that have a desirable organoleptic effect, such as a fat-mimicking effect.

Thus, there is a continuing interest for novel digestible and for novel indigestible carbohydrates, which may be used to formulate nutritional compositions or be used for preparing food supplements or pharmaceutical compositions.

DETAILED DESCRIPTION OF THE INVENTION

The inventors have found a method to prepare a specific polysaccharide that is partially digestible and partially non-digestible.

Accordingly, the present invention relates to a method for preparing a branched glucan having a chain comprising a plurality of glucose units linked by alpha 1,4-glycoside bonds and a plurality of side-groups linked to said chain via another type of glycoside bonding, which side-groups comprise one or more glucose units, the method comprising contacting a glucose source, in particular a glucose source selected from glucose, maltose and polydextrose, with a polysaccharide—which polysaccharide is a glucan (different from the branched glucan that is prepared) comprising a plurality of glucose units linked by alpha 1,4-glycoside bonds in the presence of an acid catalyst under polycondensation conditions, thereby forming the branched glucan. Said polysaccharide (used as a starting material for the preparation of the glucan that is prepared) may herein after also be referred to as the 'base glucan'. Evidently, the base glucan is different from the branched glucan that is prepared. The based glucan may be essentially linear or branched. Evidently, if it is branched it is branched to a lesser degree than the branched glucan that is to be prepared.

Further, the present invention relates to a branched glucan obtainable by a method according to the invention.

The invention further relates to a branched glucan, preferably obtainable by a method according to the invention, having a chain comprising a plurality of glucose units linked by alpha 1,4-glycoside bonds and a plurality of side-groups linked to the chain via another type of glycoside bonding, which side-groups comprise one or more glucose units, the fraction of glucose units in the side groups being at least 4% of the total amount of glucose units.

Further, the invention relates to a nutritional or pharmaceutical composition comprising a branched glucan according to the invention and one or more ingredients for nutritional products respectively pharmaceutical products.

Further, the invention relates to the use of a branched glucan according to the invention for providing both caloric value to a subject consuming the glucan and for providing soluble fibre to the subject consuming the glucan. In particular the glucan may be used to provide a prebiotic effect. Said use is generally non-medical.

Further, the invention relates to a branched glucan for use as a medicament, in particular for use in the treatment of a disorder of the gastro-intestinal tract.

Further, the invention relates to the use of a branched glucan according to the invention as a fat-mimetic in a nutritional composition. In particular, it is considered that a glucan according to the invention is suitable to impart a fat-like mouthfeel, more in particular a sensation that is similar to the sensation of fat melting in the mouth. Without being bound by theory, it is contemplated that the partial degradability of the glucan by the action of amylase in the mouth may contribute to such sensation.

A glucan (obtainable) according to the invention generally has a lower caloric value than a same weight of native starch. It generally has a higher caloric value than a same weight of a polysaccharide that is completely indigestible, such a cellulose, or polydextrose. For instance, the present invention provides a glucan having a caloric value in the range of 0.2 to 3 kcal/g, in particular of 0.4 to 2 kcal/g, more in particular about 1 kcal/g. However, in principle it is also possible in accordance with the invention to provide a glucan which is (essentially) completely indigestible by humans.

Depending upon specific method conditions (as will elaborated herein below), it is possible to prepare a branched glucan with different properties that are relevant to the behaviour of the glucan in vivo, in particular in the gastro-intestinal tract, or in (a nutritional or pharmaceutical) product before use. In particular, aspects like caloric value, digestion rate, height of blood glucose peak, viscosity, satiety effect, or prebiotic property may be modified.

A glucan according to the invention can provide both an energy source and provide a prebiotic effect. The inventors further realised that this polysaccharide is particularly interesting in that the digestible part is digested relatively slowly, compared to starch. Thus, the occurrence of undesirably high glucose plasma peak levels after consumption may be avoided, or at least reduced, compared to comparable nutritional compositions wherein the glucose for caloric intake is provided solely or to a higher extend by glucose, or quickly digested saccharides comprising glucose units (such as sucrose, starch and the like).

It is further envisaged that a branched glucan in a food or beverage can contribute to a prolonged satiety effect, after ingestion.

Moreover, in an embodiment it is envisaged that a branched glucan according to the invention can be used in a food or beverage, contributing to desirable rheological properties.

Further, a branched glucan according to the invention may be used as a humectant, a bulking agent, a Maillard promoter, a freezing point depressant (reduction of ice crystals), a flavor developer (maillard), a texturizer (volume increase). Further, the branched glucan may be used to reduce water activity.

The glucan comprising a plurality of glucose units linked by alpha 1,4-glycoside bonds and is essentially linear or branched to a lesser extent than the branched glucan that is prepared may herein after be referred to as the 'base glucan'. Usually, more than 50% of the linkages of this glucan are 1,4-glycoside bonds, in particular 80-100%, more in particular 95-100%.

It is contemplated that in the formed polymer network, the alpha 1,4 glycoside bonds mainly originate form the base glucan whereas the sugar monomers providing the branches are responsible for the formation of other linkages, in particular 1,2 linkages, 1,3 and/or 1,6 linkages. The chain or combination of chains at least conceptually derived from the base glucan may also be referred to as the backbone of the branched glucan.

The branched glucan (obtained) according to the invention is usually composed of a mixture of glucan molecules. These molecules may differ in molecular weight or branching related properties (such as number of side-groups per molecule, branching degree, type of linkage to the backbone, (average) size of the side groups).

The term "or" as used herein means "and/or" unless specified other wise.

The term "a" or "an" as used herein means "at least one" unless specified other wise.

When referring to a 'noun' (e.g. a compound, an additive etc.) in singular, the plural is meant to be included, unless specified otherwise.

The term 'glucose source' is used for a molecule providing glucose units that are used for binding glucose units to the glucan (the base glucan) by polycondensation to form the branched glucan. The glucose source is preferably selected from the group of monosaccharide glucose, maltose and polydextrose, in particular from glucose and polydextrose.

The term 'polycondensation' or 'polycondensation reaction' is generally known in the art, and used for reactions wherein molecules join together, losing one ore more (small) molecules, such as water, as by-products. The skilled person will be able to determine suitable polycondensation conditions for the preparation of the base glucan based on common general knowledge and the information disclosed herein.

With 'polymers'—in particular polysaccharides, such as glucans—are meant molecules of high relative molecular mass, the structure of which essentially comprises the multiple linkage of units derived, actually or conceptually, from molecules of low relative molecular mass (monomers). The number of linkages between the monomers in a polymer, such as a polysaccharide is generally at least 3, in particular at least 10, more in particular at least 25, at least 100, at least 500 or at least 1 000. The upper limit is not particularly critical, and may be chosen on the desired properties. The number of linkages may be up to 1 000 000 or even more, in particular 500 000 or less, more in particular 100 000 or less, 25 000 or less, or 5 000 or less, or 3 000 or less.

The term 'oligomer' is used herein for molecules of high relative molecular mass, the structure of which essentially comprises 1 to 9 linkages of units derived, actually or conceptually, from molecules of low relative molecular mass (monomers). Examples of oligomers are disaccharides (e.g. sucrose) and saccharides composed of 3 to 10 monosaccharide units, which units may be the same or different.

When referred herein to a molecular weight of a polymer, the weight average molecular weight as determined by HPLC-MALLS-RI-Viscostar (high pressure chromatography-multi angle laser light scattering-refractive index-viscometry), in particular making use of a MALLS with 18 light scattering detectors (Dawn-EOS, Wyatt Co, USA). The Viscostar is a differential pressure detector (Viscostar, Wyatt Co., USA) for measurement of intrinsic viscosity. The concentration of the eluting fractions can be measured using refractive index detector (RI2000, Germany). HPLC conditions: Gilson pump set to a flow rate of 0.6 mL/min. Samples injected at 200 µL using a Gilson autoinjector. The system fitted with two columns, namely, TSK Gel G5000PW (Japan) and a Viscotek G4000 PW XL column (Houston, Tex., USA) arranged in series. Elution with 50 mM sodium nitrate, pH 6.8 with 0.02% Na-azide added as a preservative. Analysis: A dn/dc of 0.156 for the analysis of all samples. Data analysis: ASTRA V (Version 5.3.4.14). The accuracy of the system verified using pullulan standards.

When referring to the 'caloric value' of a compound or composition, the caloric value for a human is meant.

A method according to the invention is advantageously carried out in a melt of the glucose source (in particular glucose and/or polydextrose) and the base glucan. In a method wherein the contacting under polycondensation conditions takes place in a melt, at least a substantial part of the glucose source and base glucan form part of the melt, typically more than 50 wt. %. Preferably, essentially all glucose source and base glucan are part of the melt, typically 95-100 wt. %. In particular a part of the base glucan may remain unmolten. Without being bound by theory, it is contemplated that this part of the base glucan does not significantly participate in the polycondensation reaction. It may remain in the product, thereby contributing to caloric value, or be separated from the branched glucan afterwards.

The melt further comprises the acid catalyst. Generally, also (a trace of) water is present. The presence of at least a trace of water (e.g. at least about 10 ppmw) is desired in order to let the catalyst perform its catalytic function. In view thereof, the method is carried in the presence of water, the water content preferably being at least 0.01 wt. %, in particular at least 0.1 wt. %. For allowing the acid to have catalytic effect a water concentration of less than 1 wt. %, in particular 0.5 wt. % or less generally suffices.

Further, it is contemplated that the water functions as a plasticizer, allowing a melt to be formed, in particular when a mixture consisting of the catalyst, glucose source, and the base glucan cannot form a melt (i.e. if a compound in the mixture degrades at a temperature at which such mixture is solid). Thus, in particular in the phase of the method wherein the reagents are brought together to form a reaction mixture, more in particular while a melt is being formed, the water content can advantageously be more than 1 wt. %, in particular 2 wt. % or more, more in particular 5 wt. %, e.g. up to 20 wt. %, preferably 15 wt. % or less, in particular 10 wt. % or less.

On the other hand it is generally desired that the water content is relatively low, for at least a substantial part of the method, such that no unacceptable hydrolysis of the base glucan and/or branched glucan takes place.

In an advantageous method, the contacting is initially takes place at a relatively high water content, e.g. 5-15 wt. %, in order to facilitate intimate mixing of the reagents, in particular to form a melt. Thereafter, the water content is reduced. This advantageously is realised in the course of the method, preferably while polycondensation takes place, typically by allowing the water to evaporate, and removing the water vapour from the reaction system in which the contacting takes place. Thus, the water content can be reduced gradually, e.g. to less than 1 wt. %.

The contacting under polycondensation conditions usually takes place for more than 1 min, in particular for 30 min or more, more in particular for 1 hour or more, or for 1.5 hours or more. The contacting may be continued as long as desired in order to realise the desired conversion. A contacting time under polycondensation conditions may in particular be stopped if an unacceptable colour change occurs and/or an unacceptable formation of dark spots form. A contacting time of less than 12 hours is usually sufficient, although the contacting time may be longer if desired. Preferably, the contacting time is 8 hours or less, in particular 6 hours or less, more in particular 3 hours or less. It is contemplated that longer reaction times can reduce the relative abundance of 1,4 linkages. Excessive reaction time may lead to browning. The contacting under polycondensation conditions can in particular be stopped by cooling the polycondensation reaction mixture to a temperature at which essentially no polycondensation takes place (typically to less than 100° C., in particular to about 40° C. or less, more in particular to about 20° C. or less or less.

Further, the mixture wherein base glucan, the glucose source (in particular glucose and/or polydextrose) and acid catalyst are contacted may comprise an organic plasticizer, preferably an organic plasticizer that is food grade (GRAS). The plasticizer contributes to forming a melt at a temperature where degradation of the reagents is (substantially) avoided or at least acceptably low.

In particular, the organic plasticizer may be a polyol other than a carbohydrate, more in particular a polyol be selected from the group of sugar alcohols, such as sorbitol, maltitol, xylitol, glycerol and polyethylene glycol or another polyalkylene glycol.

An organic plasticizer is preferably used to facilitate mixing the base glucan and the glucose source (in particular glucose and/or polydextrose), in particular if the ratio of the glucose source (in case of more than one glucose source is used, the total of all glucose sources taken together) to base glucan is relatively low. The total concentration of organic plasticizer(s), if present, usually is at least 0.5 wt. %, in particular at least 2 wt. %, more in particular at least 5 wt. % based on the total concentration of organic plasticizers, glucose source (in particular glucose and/or polydextrose) and base glucan. The total concentration of organic plasticizer(s), if present, usually is 20 wt. % or less, in particular 10 wt. % or less, more in particular 5 wt. % or less based on the total concentration of organic plasticizers, glucose source and base glucan. A relatively low concentration of organic plasticizers (other than a carbohydrate), can be advantageous for a technical reason or in view of food regulations.

In a specific embodiment, the sorbitol concentration is 0-5 wt. %, in particular 0-4 wt. %, based on total polyols.

In a specific embodiment the total concentration of polyols other than the glucose source (glucose, maltose, polydextrose) and polysaccharide used for the preparation of the branched glucan is 0-5 wt. %, based on total polyols, or less, in particular 0-4 wt. %.

The base glucan may in principle be any glucan, and is usually a glucan that is acceptable for use in a food application (GRAS). The base glucan is preferably selected from the group of starch, amylose, amylopectin and maltodextrins. The base glucan may be obtained be hydrolysing a larger glucan, in particular intact starch, amylose or amylopectin. Generally, the base glucan has a degree of polymerisation of at least 3 (at least 3 monomeric units per molecule). Preferably, the number average degree of polymerisation is in the range of 10 to 500 000, in particular in the range of 100 to 100 000, more in particular in the range of 250 to 25 000.

In principle the starch may originate from any source, in particular from a tuber (such as potato), root (such as tapioca) or a cereal (such as maize, wheat, rice).

Surprisingly, it is possible to use a base glucan that does not have a melting point (at 1 bara) when heated in pure form (i.e. a glucan that decomposes before a temperature is reached at which melting could occur. Generally, decomposition takes place at a temperature of about 200° C. or more. In particular, good results have been obtained with starch from potato, more in particular with a partially hydrolysed potator starch, such as partially hydrolysed potato starch sold by AVEBE under the tradename PASELLI SA2™.

The base glucan, in particular in case of a starch, preferably is gelatinised, prior to subjecting the base glucan to the polycondensation conditions (i.e. pregelatinised). Starch gelatinization is a process that breaks down the intermolecular bonds of starch molecules, typically in the presence of water and heat, allowing the hydrogen bonding sites (the hydroxyl hydrogen and oxygen) to engage more water. This irreversibly dissolves the starch granule. Suitable means of pregelatinisation are generally known in the art. Preferred means of pregelatinisation include gelatinisation in a drum-dry process and gelatinisation in a spray-dry process. In particular good results have been achieved with pregelatinised starch made in a drum-dry process.

The contacting usually takes place in a mixture in which (initially) the weight to weight ratio glucose source to the base glucan is in the range of 5:95 to 99:1, in particular in the range of 15:85 to 90:10. Evidently, if more than one glucose source and/or more than one base glucan is used, the ratio glucose source to the base glucan is the ratio of the sum of the amounts of glucose sources to the sum of the amounts of the base glucans.

A preferred ratio depends on desired properties of the branched products, such as digestion related properties, rheological properties or ratio of glucose units in the side-chains to glucose in the backbone. Moreover, a relatively high initial glucose content is in particular advantageous to facilitate contacting under polycondensation conditions with the base glucan, also in the absence of an organic plasticizer or in the presence of a relatively low amount of plasticizer.

Preferably, (initially) the weight to weight ratio glucose source (in particular glucose and/or polydextrose) to the base glucan is 20:80 or more, more preferably 30:70 or more. For facilitating mixing, the ratio preferably is 45:55 or more, especially if glucose is the only glucose source or the major glucose source (more than 50 wt % of the glucose source).

Usually, the weight to weight ratio glucose source (in particular glucose and/or polydextrose) to the base glucan is 90:10 or less, preferably 80:20 or less, more preferably 70:30 or less, in particular 65:35 or less, more in particular 60:40 or less.

A ratio in the range of 40:60 to 60:40, in particular in the range of 45:55 to 55:45 is in particular preferred, especially for glucose as the only or major glucose source.

The glucose source and base glucan taken together usually form 70 wt. % or more of the mixture wherein the contacting takes place, preferably at least 80 wt. % of the mixture, in particular at least 90 wt. % of the mixture. At least at the start of the polycondensation, the glucose source and base glucan taken together usually form less than 99.5 wt. % of the mixture, in particular 98 wt. % or less, more in particular 95 wt. % or less.

The balance is usually formed by at least the acid catalyst and at least a trace of water. Optionally, a minor amount of one or more other components, in particular one or more other biomolecules, such as proteins and other polypeptides, fatty acids (e.g. in glycerides or phospholipids), may be present. If present, the total concentration of other components is usually less than 10 wt. %, in particular less than 5 wt. %, more in particular less than 1 wt. %.

As a catalyst, in principle any acid catalyst capable of catalysing the reaction of the glucose source with the base glucan can be used, in particular any food-grade (GRAS) acid catalyst. A preferred catalyst is an organic acid, in particular citric acid.

An inorganic acid may also be used as a catalyst. If an inorganic acid is used, generally an inorganic acid catalyst other than HF is used. A preferred inorganic acid is phosphoric acid, which is considered to catalyse with an advantageous selectivity.

The catalyst is usually present in a (total) concentration of 0.1-5 wt. %, preferably in a concentration of 0.1-2 wt. %.

A method according the invention may suitably be carried out at a temperature in the range of 100 to 250° C., preferably in the range of 120 to 220° C., in particular in the range of 140 to 190° C. Evidently, in case the reaction is carried out in a melt, the temperature is above the melting temperature of the mixture. A relatively low temperature is in particular preferred for reducing the tendency of the carbohydrate components to degrade. A relatively high temperature is in particular preferred in view of reaction rate (in particular for 1,6 linkage), reduced viscosity during the contacting.

Usually, the contacting under polycondensation conditions takes place at a pressure below the partial water vapour pressure under said contacting conditions. This allows water formed during the polycondensation to be removed from the mixture wherein base glucan and glucose are contacted. This is advantageous for selectivity and/or conversion rate. Preferably, said pressure is a sub-atmospheric pressure, at least after start of the polycondensation, in particular a pressure of 0.5 bar or less. The lower limit of the pressure is not critical, and may be determined by the equipment used. E.g., the pressure may be 1 mbar or more, in particular 10 mbar or more.

After preparation of the branched glucan, the prepared branched glucan can be recovered from the contacting mixture based on methodology known per se in the art.

In a specific embodiment, the recovery comprises a precipitation step using a solvent for one or more of the following: unreacted glucose, catalyst, plasticizer if present) other low molecular weight compounds, polysaccharide having a relatively low molecular weight (such as degraded (base-)glucan), in which solvent the branched glucan or at least most of it) precipitates. Examples of such solvents are polar organic solvents like ethanol. Alternatively or in addition size-based recovery step may be used such as size exclusion chromatography, or dialysis with a molecular weight cut-off filter, which typically will have a molecular weight cut of below the lowest molecular weight of interest for the branched glucan. For the size-based separation step, the glucan is usually dissolved, e.g. in water and then purified in the size-based separation step, The liquid comprising the purified glucan can be processed in a manner known per se, e.g. spray dried.

The recovered branched glucan, may be used for formulating a nutritional product without needing to remove unreacted base glucan (if any is still present). If present, the unreacted base glucan typically contributes to the caloric value.

If desired, the mixture obtained after polycondensation, or the recovered glucan product comprising the branched glucan may be subjected to a selective hydrolysis, in particular an enzymatic hydrolysis, to modify a product property, such as a digestion or fermentation related property. For this, conditions may be used as are known in the art for the specific enzyme used. In particular, the product may be subjected to hydrolysis in a reaction catalysed by an alpha-amylase. Thus, the number of alpha 1,4 glycoside linkages is reduced and digestible parts of a branched glucan molecule may be cleaved from indigestible parts. This process reduces the average molecular weight of the product. Also glucose, maltose and relatively small glucose polymers may be formed, which may increase the digestion rate of the product, if not removed. However, by removal of this glucose and optionally glucose oligomers (e.g. by precipitation and/or dialysis as described above) a branched glucan product may be obtained of which a lower part is digestible than the product before enzymatic hydrolysis, thereby making a larger part (or the whole glucan) available for use as a dietary fibre, such as a prebiotic.

A branched glucan according to the invention, including a branched glucan obtained in a method according to the invention, may differ from known glucans in one or more ways. In particular, the difference may reside in one or more of the following:
  branching characteristics, such as branching degree (relative number of glucose units in the chain to which a side-group is attached); average size of the side-chains; abundance of specific types of glycoside bonds
  average molecular weight
  molecular weight distribution
  rheological properties, such as viscosity (cf. to other glucans with same molecular weight)
  hydrodynamic radius
  digestibility in general
  resistance to degradation by enzymatic hydrolysis in the presence of a specific enzyme capable of catalysing the hydrolysis of a polysaccharide, such as an alpha amylase.

Exact properties may vary. In particular one or more of the following applies.

An indication of differences in branching characteristics can be obtained by comparing Mark-Houwink Sakurada (MHS) plots of a branched glucan according to the invention and another glucan. As a rule of thumb, a branched glucan according to the invention is generally more dense than a comparable glucan (similar molecular weight+molecular weight distribution, similar polymer configuration) that is unbranched or branched to a less extent.

In a branched glucan (obtained in a method) according to the invention, glucose units may be linked to the base glucan via an alpha 1,6 glycoside bond, an alpha 1,2 glycoside bond or an alpha 1,3 glycoside bond.

In a glucan (prepared according to) the invention (substantially) all the side-groups may be bound via one type of bonds, in particular alpha 1,6 glycoside bond. Alternatively, a (substantial) part of the side-groups may be bound via one type of bonds and a (substantial part of the) side groups may be bound via a different type of bounds.

A branched glucan (obtained by a method) according to the invention has a chain (a backbone, which may be a branched or crosslinked structure) comprising a plurality of glucose units linked by alpha 1,4-glycoside bonds. This chain usually at least essentially consists of a plurality of glucose units. This chain usually at least essentially consists of a plurality of glucose units linked by alpha 1,4-glycoside bonds, although in practice a minor number of the linkages, generally 4% or less may be linked via another type of glycoside linkage, typically depending on the base material on which the branched glucan has been prepared.

The branched glucan contains a plurality of side-groups linked to the backbone via another type of glycoside bonding, which side-groups comprise one or more glucose units. The fraction of glucose units in the side groups can be determined by subjecting the glucan to enzymatic digestion (alpha 1,4 amylase) and using gel permeation chromatography to analyse the fragments. The fraction of glucose units in the side groups usually is at least 4% of the total amount of glucose units, in particular 10% or more, more in particular 20% or more, 25% or more, 30% or more, 35% or more, 40% or more or 50% or more. The fraction of glucose units in the side groups usually is 95% or less of the total amount of glucose units, in particular 90% or less, more in particular 80% or less, 75% or less, 70% or less, 65% or less, or 60% or less.

When preparing a branched glucan according to the invention in a method according to the invention, molecular weight of the base glucan, other size-related features of the base glucan, such as molecular weight distributions, polydispersity, ratio glucose source (in particular glucose and/or polydextrose) to base glucan and other conditions under which the preparation is carried out may have an effect on the properties the branched glucan.

The molecular weight of the branched glucan usually is more than 10 kg/mol, in particular 100 kg/mol or more, preferably 500 kg/mol or more, in particular at least 750 kg/mol or more. The molecular weight of the branched glucan usually is 10 000 kg/mol or less, in particular 5 000 kg/mol or less more in particular 2 500 kg/mol or less.

The branched glucan may have a monomodal or polymodal molecular weight distribution, in particular a bimodal molecular weight distribution, as can be determined by size exclusion chromatography. In a method of the invention, a branched glucan product with a polymodal molecular weight distribution may in particular be obtained at a relatively low ratio glucose source to base glucan.

A branched glucan according to the invention generally comprises chain segments having a chain length of 3 glucose units or more that are not enzymatically hydrolysed to form glucose or maltose in the presence of alpha-amylase, at least not when subjected to hydrolytic conditions, as mentioned in the examples. It is contemplated that these chains typically comprise one or more glucose side chains. In particular, the branched glucan comprises such chain segments which comprise at least 5 glucose units, more in particular at least 15 glucose units or at least 25 glucose units. The upper limit of those non-hydrolysed segments is determined by the length of the non-hydrolysed branched glucan and its branching characteristic and may be a 100 or more. In particular, after subjecting the branched polymer to enzymatic digestions branched glucan segments comprising 75 glucose units or less, more in particular 50 glucose units or less, or 30 glucose units or less may remain.

In terms of molecular weight, it has been found possible to provide a branched glucan which after enzymatic hydrolysis under conditions as mentioned in the examples has a residual weight average molecular weight of more than 1 000 g/mol, in particular of 5 000 g/mol or more. The residual weight average molecular weight may in particular be up to about 10 000 g/mol, although higher average molecular weights are considered to be feasible, e.g. of up to 20 000 g/mol, or up to 40 000 g/mol.

The branched glucan according to the invention generally comprises resistant carbohydrate. Usually, the resistant fraction is 5 wt. % or more, preferably 10 wt. % or more, in particular 15 wt. % or more, more in particular 20 wt. % or more, more in particular 30 wt. % or more. The branched glucan may consist of resistant carbohydrate. Preferably, the resistant carbohydrate fraction is 98 wt. % or less, in particular 90 wt. % or less, more in particular 80 wt. % or less. The resistant fraction can be determined by the methodology as described in the examples.

In a preferred embodiment, in particular if it is desired that the glucan has a desirable organoleptic effect, such as a fat-mimicking organoleptic effect, the glucan is resistant for 98 wt. % or less, in particular for 5-90 wt. %, more in particular for 10-80 wt. % to hydrolysis by human fraction is salivary alpha amylase in a test as described in the examples, except that human salivary alpha amylase is used.

The branched glucan may be used as an ingredient of a nutritional or pharmaceutical composition to provide caloric value and/or to provide dietary fibre, in particular a dietary fibre with prebiotic effect. In thick-viscous fluids or gels the branched glucan may also serve as a thickening or gelling agent.

In an embodiment, the nutritional composition according to the invention is a solid product (dimension stable at 20° C. in the absence of applied pressure). In a specific embodiment, the product is a paste at ambient temperature (20° C.).

In an embodiment the nutrition is a fluid product at ambient temperature (20° C.).

The nutritional composition may be selected from beverage and other food compositions. For example, the nutritional composition may be a sports drink, health drinks. Other examples include dairy products and dairy-substitute products; desserts, e.g. puddings, mousses, creams, ice-cream, fruit-ice; clinical foods; bakery products, e.g. cookies, cake, muffins; chewing gum; confectionery, e.g. candy, chocolate; dressings, e.g. salad dressings; sauces, e.g. sweet sauces; spreads, e.g. fruit spreads; processed fruit products.

The pharmaceutical composition may in particular be a composition for use in a prophylactic or therapeutic treatment of a disorder of the gastro-intestinal tract, e.g. stool-related problems. The pharmaceutical composition may essentially consist of the branched glucan, or contain one or more ingredients known per se for formulating a pharmaceutical compositions, such as excipients, colourings, flavourings, coatings.

The nutritional or pharmaceutical composition is usually consumed orally or otherwise administered to the gastro-intestinal tract enterally, such as by tube feeding. A daily dosage of the branched glucan can readily be determined based on the body weight of the subject and recommended dosages for other carbohydrates. For an adult human, a daily dosage of branched glucan will usually be in the range of 0.1 mg to 100 mg per kg body weight, in particular 1 mg to 75 mg per kg body weight, more in particular 5 to 70 mg per kg body weight.

The branched glucan, nutritional or pharmaceutical composition is in particular suitable for administration to a human. Other animals to which the branched glucan, nutritional or pharmaceutical composition in particular include other mammals, more in particular pets, such as dogs, and animals used in agriculture (lifestock).

The invention will now be illustrated by the following examples.

EXAMPLE 1

Material

Paselli SA2 (Avebe, Netherlands), derived from the enzymatic hydrolysis of potato starch, was added to a conventional polydextrose recipe (see methods for details). Paselli P (AVEBE, Netherlands) is an instant native starch. The polydextrose recipe was made using D+glucose (Sigma-Aldrich, USA) and sorbitol (sigma-Aldrich, USA). Citric acid (Sigma-Aldrich, USA) company was also added to this mixture.

Enzymatic hydrolysis was made using alpha amylase, Termamyl 120 (Novozymes, Denmark) and amyloglucosidase from *Aspergillus niger* (Megazyme, Ireland)

Equipment:

The polycondensation reaction was conducted using a Heidolph Laborata 4000 efficient rotary evaporator (rotavap) fitted with a diaphragm-vacuum pump (Vacubrand, Germany). After heat treatment, the samples were pulverized using a mortar and pestle.

Procedure

About 100 grams of the mixture was dry blended in a 1 L round bottom flask. The flask was placed on the rotavap and lowered into an oil bath pre-heated to 180° C. for a certain amount of time. The reaction took place under vacuum conditions (100 mPa). The reaction was finished by removal of the flask out of the oil bad.

Experiments 1-21

Melting Behaviour Instant Starch and Glucose

The following formulations and conditions were chosen out:

TABLE 1 melting behaviour Paselli SA2 in glucose at 180° C.

| nr. | glucose wt % | Paselli SA2 wt % | temperature ° C. | melting |
|---|---|---|---|---|
| 1 | 100 | 0 | 180 | yes |
| 2 | 90 | 10 | 180 | yes |
| 3 | 80 | 20 | 180 | yes |
| 4 | 70 | 30 | 180 | yes |
| 5 | 60 | 40 | 180 | yes |
| 6 | 50 | 50 | 180 | yes |
| 7 | 40 | 60 | 180 | no |

At a substitution level of 60% by the pre-gelatinized starch no melting phase was observed under these conditions. At 50% a melting phase was observed.

Similar tendencies are found when the reaction was conducted at 165° C. (table 2)

TABLE 2 melting behaviour Paselli SA2 in glucose at 165° C.

| nr. | glucose wt % | Paselli SA2 wt % | temperature ° C. | melting |
|---|---|---|---|---|
| 8 | 100 | 0 | 165 | yes |
| 9 | 90 | 10 | 165 | yes |
| 10 | 80 | 20 | 165 | yes |
| 11 | 70 | 30 | 165 | yes |
| 12 | 60 | 40 | 165 | yes |
| 13 | 50 | 50 | 165 | yes |
| 14 | 40 | 60 | 165 | no |

It was observed that the melting time was longer when the reaction was carried out at 165° C. in comparison to the ones that were done at 180° C.

TABLE 3 melting behaviour Paselli P in glucose at 180° C.

| nr. | glucose wt % | Paselli P wt % | temperature ° C. | melting |
|---|---|---|---|---|
| 15 | 100 | 0 | 180 | yes |
| 16 | 90 | 10 | 180 | yes |
| 17 | 80 | 20 | 180 | yes |
| 18 | 70 | 30 | 180 | yes |
| 19 | 60 | 40 | 180 | yes |
| 20 | 50 | 50 | 180 | yes |
| 21 | 40 | 60 | 180 | no |

The melting behaviour for Paselli P in glucose is identical, under these conditions, to Paselli SA2.

Experiments 22&23

Polycondensation Reactions

The following conditions were applied:

TABLE 4 polcondensation reactions

| nr. | glucose % | glucose g | Paselli SA2 g (ds) | citric acid g | sorbitol g | temperature ° C. | time h |
|---|---|---|---|---|---|---|---|
| 22 | 100 | 89.0 | — | 1 | 10 | 180 | 2 |
| 23 | 50 | 44.5 | 44.5 | 1 | 10 | 180 | 2 |

Molecular weight and digestibility was determined.

Molecular Weight Determination:

100 mg grinded sample was solved into 10 ml 0.1M Na-phosphate buffer (pH 7+0.02% Na-azide (HPLC eluens). 1 ml of transferred in an HPLC vial. Two TSKgel GMPW×1 columns (7.5 mm×30 cm) in series were used in conjunction with a pre-column of the same type (7.5 mm×7.5 mm). The columns were eluted with 0.1M Na-phosphate buffer pH7+ 0.02% Na-azide at a pump speed of 1 ml/min. 20 µl sample was injected. A waters 410 RI detector was used.

Digestibility was Analysed by Use of the Following Procedure:

250 mg sample was dissolved in 10 ml 5 mM Na-maleate buffer (pH6). Tot his buffer solution 50 µl Thermamyl (Sigma A3403) en 10 µl AMG (Megazyme E-AMGDF) was added. After 2 hours incubation at 60° C. (stirring) 62 µl 2M HAc was added. 20 µl of this solution was used for the HPLC analyses.

HPLC Analysis:

Two TSK gel 2500xl columns (7.5 mm×30 cm) in series were used. These columns were eluted with milli Q at 80° C. with a flow of 0.5 ml/min. A waters 2414 RI detector was used for detection.

Figure 1:
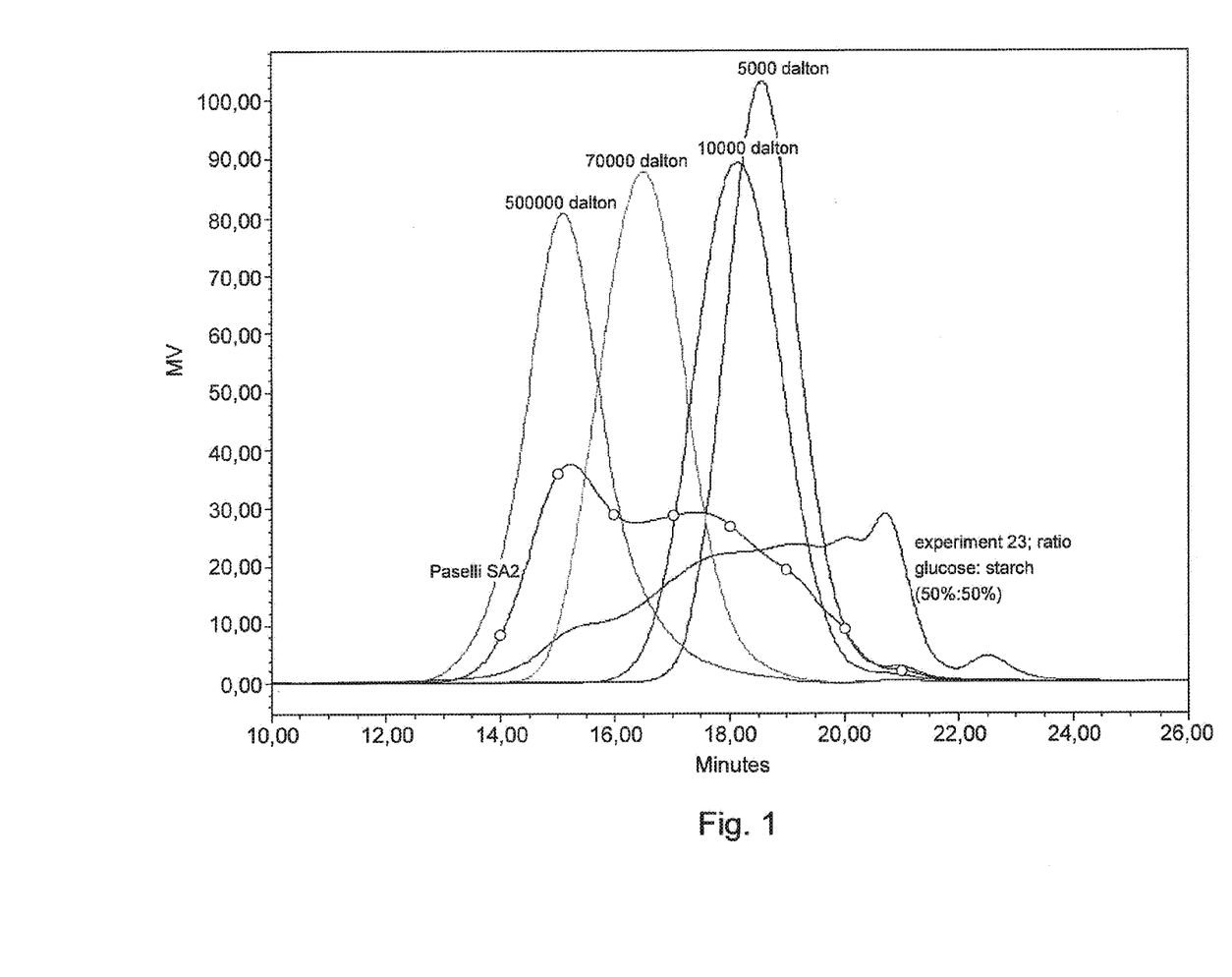
FIG. 1 shows chromatograms of several standards and a polycondensation product obtainable in accordance with the invention (experiment nr 23). By use of the standards one is able to get an indication of the molecular weight (& distribution). One can clearly see that the average molecular weight of the polycondensation product (nr 23) is lower than that of the base glucan (Paselli Sa2). This indicates that hydrolysis took place during the reaction.
Figure 2:
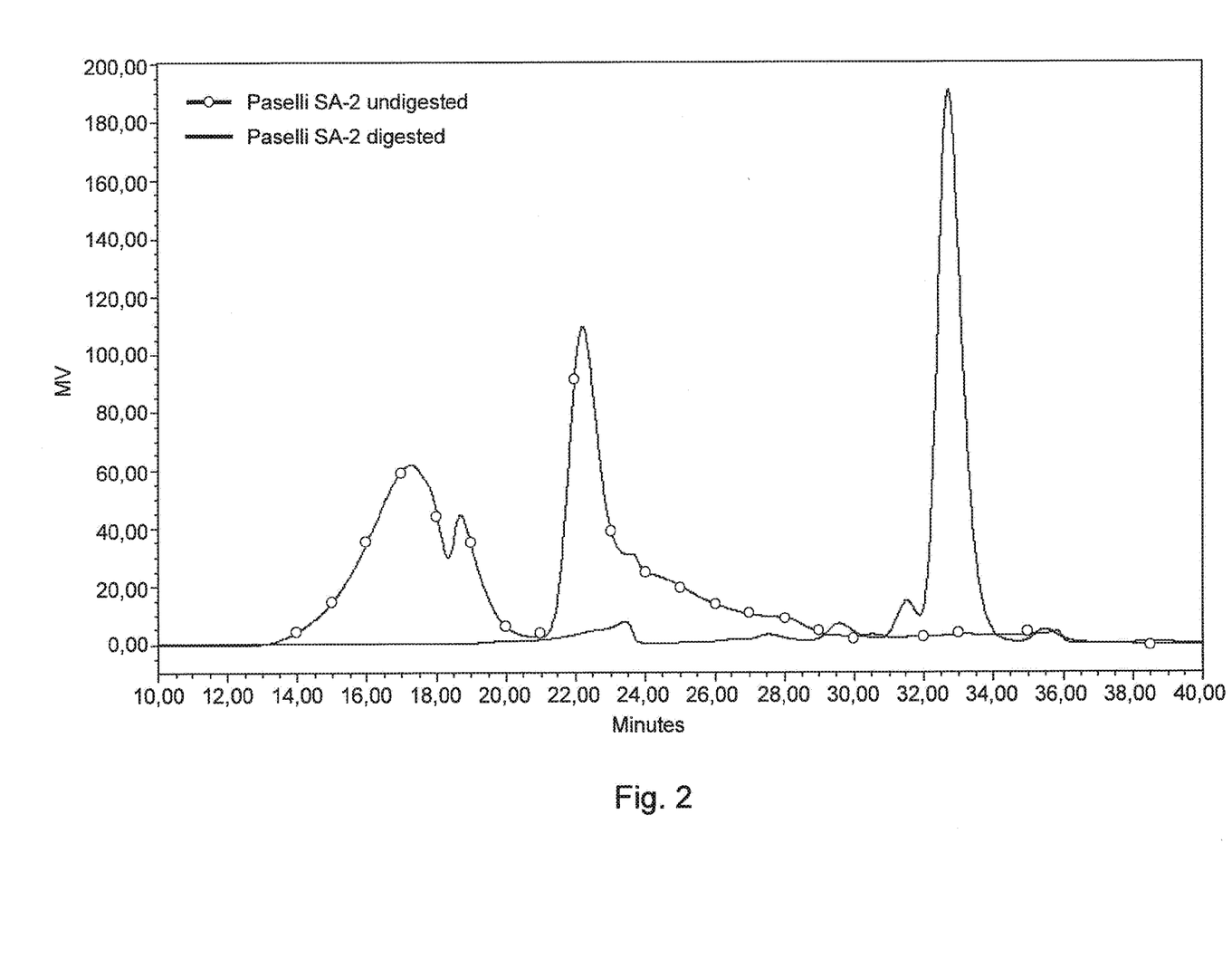

FIG. 2 shows chromatograms of Paselli SA2 before and after digestion (providing a digestibility profile). After digestion with amylase and amyloglucosidase, 99% of the starting material was converted into glucose.

Figure 3:
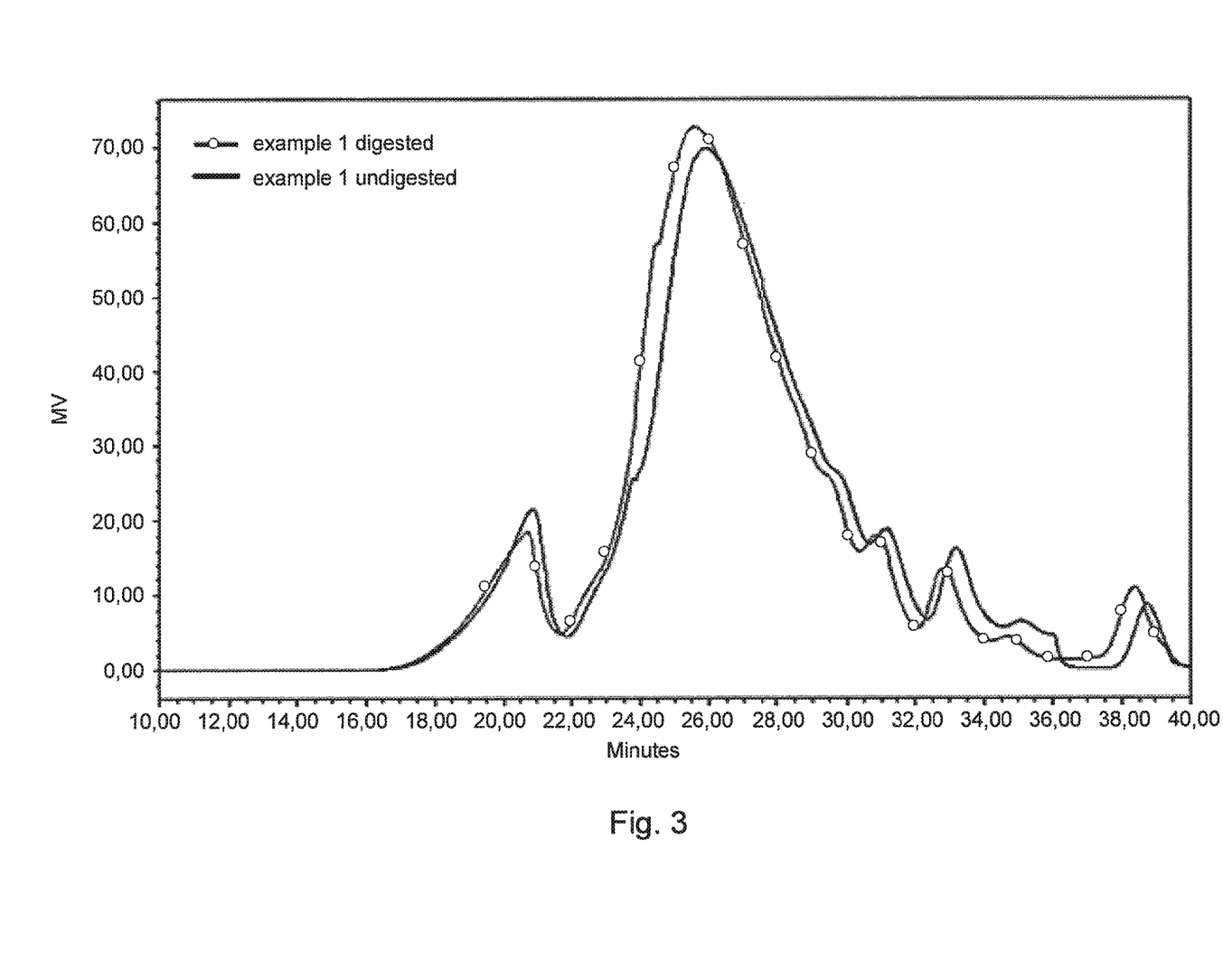

FIG. 3 shows a digestibility profile of the glucan obtained by experiment nr. 22 sample 22 (polydextrose). This Figure shows that no significant digestion of polydextrose took place.

Figure 4:
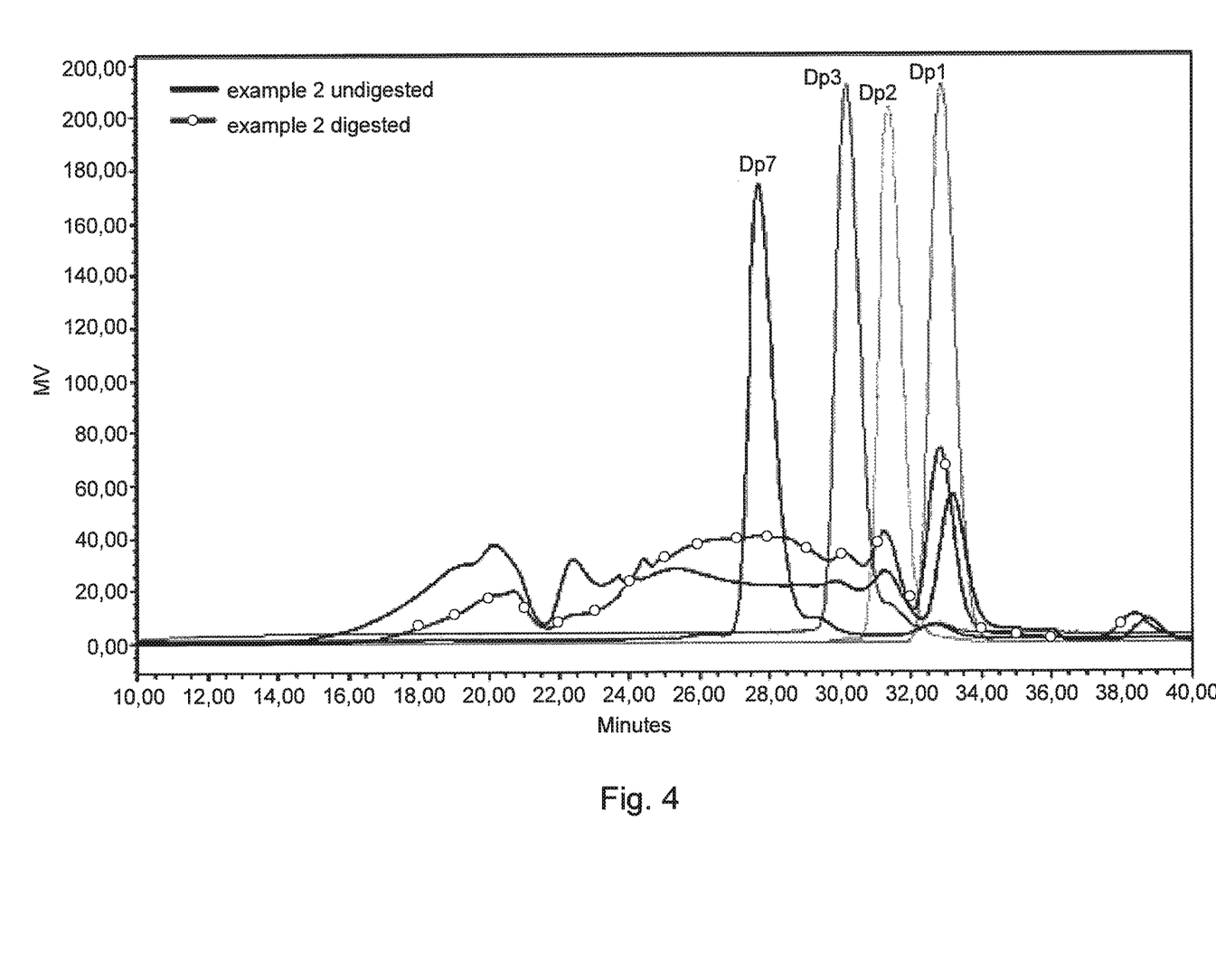

FIG. 4 shows a digestibility profile of a glucan according to the invention (experiment nr 23; mixture glucose/Paselli). The digestibility profile is clearly distinct from that of the base glucan (Paselli SA2) and of polydextrose. In comparison with polydextrose, enzymatic hydrolysis takes place. By comparing the undigested sample with the one that is digested, we can clearly see that besides glucose, resistant starch structures are formed.

In comparison with "standard" polydextrose (experiment 22) it is observed that higher levels of low molecular weight (DP2 to DP10) resistant oligosaccharides are formed after digestion.

Concluding Observations to the Examples

A glucan (such as Paselli SA2) is able to participate in a polycondensation reaction with glucose;

the inclusion a glucan in a polycondensation reaction with glucose results in a product that has increased resistance to alpha-amylase and amyloglucosidase, at least relative to the glucan before subjecting it to the reaction; and that a different digestibility profiles arise from the alpha-amylase and amyloglucosidase hydrolysates of such a mixture subjected to a polycondensation process.

The invention claimed is:

1. Method for preparing a branched glucan having a chain comprising a plurality of glucose units linked by alpha 1,4-glycoside bonds and a plurality of side-groups linked to said chain via another type of glycoside bonding, which side-groups comprise one or more glucose units, the method comprising
    providing a melt comprising a glucose source selected
        from the group consisting of glucose, maltose and polydextrose with a polysaccharide
        wherein said polysaccharide
            is a glucan comprising a plurality of glucose units linked by alpha 1,4-glycoside bonds, which glucan is essentially linear or branched to a lesser extent than the branched glucan that is to be prepared,
            has a number average degree of polymerisation of at least 10, and
            has been gelatinized prior to providing the melt, wherein the weight to weight ratio of the total of said glucose source to said polysaccharide in the melt being in the range of 30:70 to 99:1, and contacting said glucose source and said polysaccharide in the melt in the presence of an acid catalyst under polycondensation conditions, thereby forming the branched glucan.

2. Method according to claim 1, wherein the contacting takes place at a temperature in the range of 100 to 250° C.

3. Method according to claim 1, wherein the contacting takes place in the presence of water.

4. Method according to claim 1, wherein said polysaccharide that is contacted is selected from the group consisting of starches and maltodextrins.

5. Method according to claim 1, wherein the contacting takes place in a mixture in which initially the weight to weight ratio of the total of said glucose source to said polysaccharide is in the range of 30:70 to 99:1, said components together forming at least 70 wt. % of the mixture.

6. Method according to claim 1, wherein the contacting takes place under a sub-atmospheric pressure.

7. Method according to claim 1, wherein at least a part of the side-groups are linked to the chain via a 1,6 glycoside bond, a 1,2 glycoside bond or a 1,3 glycoside bond.

8. Method according to claim 1, wherein said polysaccharide contacted with the glucose source has a number average degree of polymerisation in the range of 10-500 000.

9. Method according to claim 8, wherein said polysaccharide has a number average degree of polymerisation in the range of 100 to 100 000.

10. Method according to claim 9, wherein said polysaccharide has a number average degree of polymerisation in the range of 250 to 25 000.

11. Method according to claim 1, wherein the glucose source is glucose, maltose or a mixture thereof.

12. Method according to claim 1, wherein the glucose source is glucose.

13. Method according to claim 5, wherein in the mixture initially the weight to weight ratio of the total of said glucose source to said polysaccharide is in the range of 50:50 to 80:20, said components together forming at least at least 90 wt. % of the mixture.

14. Method according to claim 6, wherein the contacting under polycondensation conditions takes place at a pressure below the partial water vapour pressure of less than 0.5 bar.

15. Method according to claim 1, wherein said glucose source, said polysaccharide and said catalyst are intimately mixed at a relatively high water content to form a melt and thereafter water content is reduced.

16. Method according to claim 3, wherein the contacting under polycondensation conditions is carried out in a reaction system from which water is removed by allowing the water to evaporate and remove the water from the reaction system.

17. Method according to claim 1, wherein the contacting under polycondensation conditions takes place for a duration in the range of more than 1 min to less than 12 hours.

18. Method according to claim 4, wherein the polysaccharide is a starch from a tuber or root.

19. Method according to claim 18, wherein the polysaccharide is a starch from potato.

* * * * *